(12) United States Patent
Wang

(10) Patent No.: US 11,771,548 B2
(45) Date of Patent: Oct. 3, 2023

(54) SURGICAL INSTRUMENT

(71) Applicant: BUDDHIST TZU CHI MEDICAL FOUNDATION, Hualien (TW)

(72) Inventor: Chen-Chie Wang, Hualien (TW)

(73) Assignee: BUDDHIST TZU CHI MEDICAL FOUNDATION, Hualien (TW)

( * ) Notice: Subject to any disclaimer, the term of this patent is extended or adjusted under 35 U.S.C. 154(b) by 185 days.

(21) Appl. No.: 17/224,665

(22) Filed: Apr. 7, 2021

(65) Prior Publication Data
US 2022/0323197 A1  Oct. 13, 2022

(51) Int. Cl.
  *A61F 2/08* (2006.01)
  *A61B 17/04* (2006.01)
  *A61B 17/00* (2006.01)

(52) U.S. Cl.
  CPC ........ *A61F 2/0805* (2013.01); *A61B 17/0469* (2013.01); *A61B 2017/00238* (2013.01)

(58) Field of Classification Search
  CPC .................. A61F 2/0805; A61B 17/0469
  See application file for complete search history.

(56) References Cited

U.S. PATENT DOCUMENTS

| | | | | |
|---|---|---|---|---|
| 5,242,458 A | * | 9/1993 | Bendel | A61B 17/2909 606/147 |
| 7,232,446 B1 | * | 6/2007 | Farris | A61B 17/06166 112/169 |
| 11,399,822 B2 | * | 8/2022 | Huntington | A61B 17/0625 |
| 2007/0270885 A1 | * | 11/2007 | Weinert | A61B 17/0483 606/139 |
| 2016/0367243 A1 | * | 12/2016 | Martin | A61B 17/06133 |
| 2018/0116652 A1 | | 5/2018 | Torrie | |
| 2021/0204934 A1 | * | 7/2021 | Huntington | A61B 17/0625 |

FOREIGN PATENT DOCUMENTS

| | | |
|---|---|---|
| CN | 106456155 A | 2/2017 |
| TW | M471856 U | 2/2014 |

* cited by examiner

*Primary Examiner* — Phong Son H Dang
(74) *Attorney, Agent, or Firm* — Melissa Hunter-Ensor; Leslie Serunian; Greenberg Traurig, LLP

(57) ABSTRACT

Provided is a surgical instrument including a first holding member, a sleeve member, a linkage member, a second holding member, a hook member and an opening/closing member. The second holding member is pivotally connected to the first holding member and when the second holding member moves relative to the first holding member, the linkage member is moved inside the sleeve member so as to drive the opening/closing member to move relative to the hook member. Through the movement of the opening/closing member of the surgical instrument, surrounding soft tissues, blood vessels or nerves that have strayed into the hook member can be pushed out so as not to be damaged by the hook member during surgery.

13 Claims, 10 Drawing Sheets

SURGICAL INSTRUMENT

BACKGROUND

1. Technical Field

The present disclosure relates to surgical instruments, and more particularly, to a surgical instrument used for minimally invasive tendon repair surgery.

2. Description of Related Art

With the development of science and technologies, minimally invasive surgery has become a trend in clinical medicine. Minimally invasive surgery can effectively reduce injury to patients, and has advantages of smaller wound, faster recovery, less muscle or nerve damage, lower anesthesia risk, shorter operation time, lower infection rate and so on.

Accordingly, there are high demands on surgical instruments used in minimally invasive surgery, and a variety of surgical instruments have been developed. For example, Taiwan Patent No. M471856 discloses a suture holding device; U.S. Patent Publication No. 2018/0116652A1 discloses a suture passer and grasper instrument; and China Patent Publication No. 106456155A discloses a suture passer, which facilitates doctors to hold a suture for piercing and suturing.

However, when the above-mentioned surgical instruments are used in ultrasound-guided minimally invasive surgery, such as minimally invasive Achilles tendon repair surgery, they may injure surrounding soft tissues, blood vessels or nerves during the operation when the movable mechanism is used to prevent a suture from falling off after capturing the suture. For example, in the suture holding device disclosed by Taiwan Patent No. M471856, when a first holding portion and a second holding portion are closed, surrounding soft tissues, blood vessels or nerves that have strayed into the suture holding portions in operation may be damaged. Further, in the suture passer and grasper instrument disclosed by U.S. Patent Publication No. 2018/0116652A1, when a suture is captured by two wire-like arms, surrounding soft tissues, blood vessels or nerves may also be captured. In the suture passer disclosed by China Patent Publication No. 106456155A, when a suture snare retracts, its hook end may capture surrounding soft tissues, blood vessels or nerves.

Therefore, one of the unmet needs is a surgical instrument that resolves the above-described drawbacks and problems.

SUMMARY

In view of the foregoing, the present disclosure provides a surgical instrument, which comprises: a first holding member; a sleeve member, one end of which is coupled to the first holding member; a linkage member disposed inside the sleeve member and having a first end and a second end, wherein the first end is positioned inside the first holding member; a second holding member pivotally connected to the first holding member and coupled to the first end of the linkage member, such that the linkage member moves inside the sleeve member when the second holding member moves relative to the first holding member; a hook member comprising an extending portion and a bending portion, wherein one end of the extending portion is coupled to the other end of the sleeve member, and the bending portion extends from the other end of the extending portion and bends, where an opening is configured between said one end of the extending portion coupled to the sleeve member and a free end of the bending portion; and an opening/closing member having one end pivotally connected to the extending portion and connected to the second end of the linkage member such that when the linkage member moves, the other end of the opening/closing member moves between the extending portion and the opening.

In at least one embodiment, when the second holding member moves away from the first holding member, the opening/closing member moves toward the extending portion.

In at least one embodiment, the extending portion further comprises a receiving space recessed inside the extending portion for receiving the opening/closing member.

In at least one embodiment, when the second holding member moves toward the first holding member, the opening/closing member moves toward the opening.

In at least one embodiment, the opening/closing member moves toward the opening until one end of the opening/closing member abuts against the free end of the bending portion.

In at least one embodiment, the opening/closing member comprises a pivoting portion pivotally connected to the hook member and an opening/closing portion extending from the pivoting portion along a tangent direction thereof and having a length that allows the opening/closing portion to abut against the free end of the bending portion.

In at least one embodiment, the linkage member is pivotally connected at a position deviating from the position where the pivoting portion is pivotally connected to the hook member such that when the linkage member moves, the opening/closing portion rotates relative to the hook member by an angle between 0 and 40 degrees.

In at least one embodiment, the surgical instrument further comprises a connection member between the linkage member and the pivoting portion, wherein two ends of the connection member are respectively pivotally connected to the linkage member and to the pivoting portion at a position deviating from the position where the pivoting portion is pivotally connected to the hook member, thereby maintaining the linkage member in an axial direction parallel to the sleeve member.

In at least one embodiment, the first holding member comprises a first engaging portion having a first tooth portion, and the second holding member comprises a second engaging portion having a second tooth portion; when the second holding member moves toward the first holding member, the second tooth portion of the second engaging portion is engaged with the first tooth portion of the first engaging portion.

In at least one embodiment, an angle between the hook member and the sleeve member is in a range of from 135 to 225 degrees.

In at least one embodiment, an angle between the sleeve member and the first holding member is in a range of from 135 to 225 degrees.

In at least one embodiment, the first holding member and the second holding member are made of plastic for medical use; the sleeve member is made of plastic or stainless steel for medical use; the hook member and the opening/closing member are made of stainless steel for medical use; and the linkage member is made of stainless steel for medical use.

In at least one embodiment, the linkage member is a rod, a wire or a spring.

According to the present disclosure, when the first holding member and the second holding member move relative to one another, the opening/closing member can move between the extending portion and the opening. As such, after a suture is captured by the hook member, the opening can be closed by the opening/closing member, thus preventing the suture from falling off and also pushing out the surrounding soft tissues, blood vessels or nerves that have strayed into the opening. Therefore, the surgical instrument of the present disclosure overcomes the conventional drawbacks of injuring surrounding soft tissues, blood vessels or nerves and at least has advantages of short recovery time after surgery, low infection rate, small wound, short operation time, short training time, among others.

DETAILED DESCRIPTION

The following embodiments are provided to illustrate the present disclosure, these and other advantages and effects will be apparent to those skilled in the art after reading this specification. The present disclosure can be implemented and applied through other embodiments.

The present disclosure discloses a surgical instrument applicable to minimally invasive surgery, e.g., to a tendon repair surgery for such as Achilles tendon, rotator cuff, quadriceps and so on, but not limited thereto. Further, the surgical instrument of the present disclosure can be used in combination with imaging devices such as ultrasounds and endoscopes so as to facilitate doctors to accurately locate injuries.

Figure 1A:
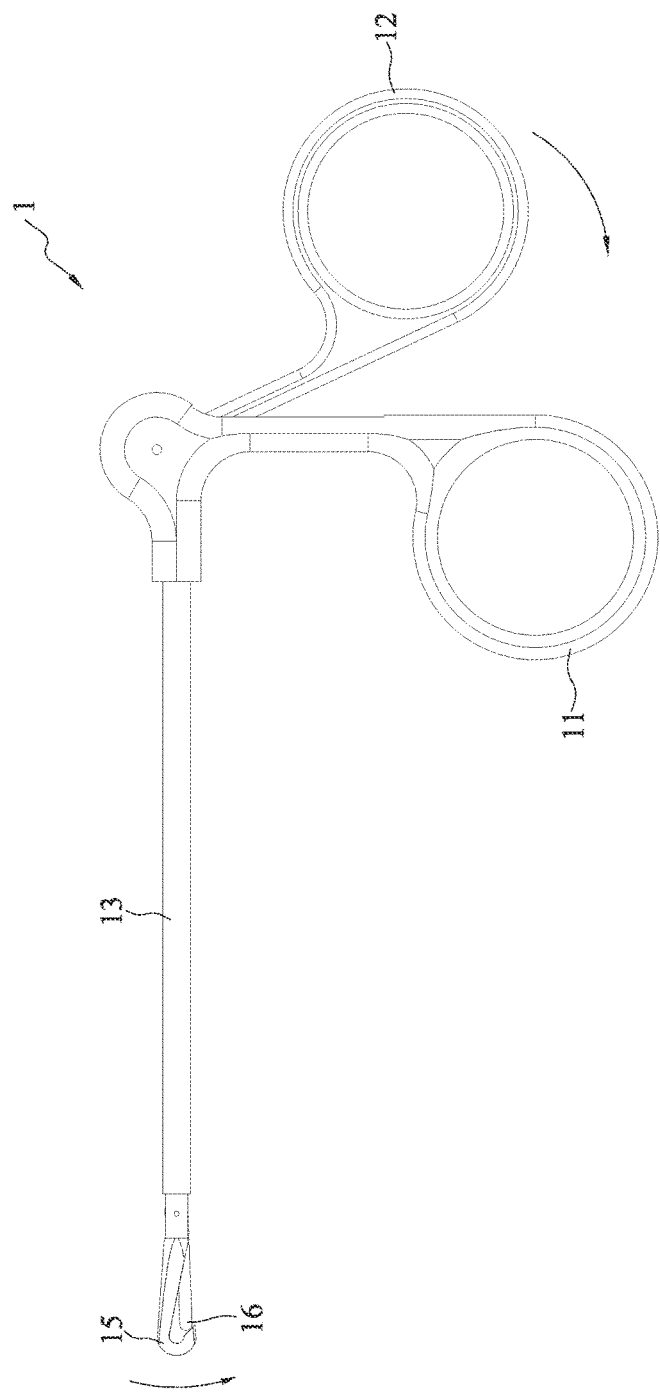
FIG. 1A is a schematic overall view of a surgical instrument in a first operation state according to the present disclosure.
Figure 1B:
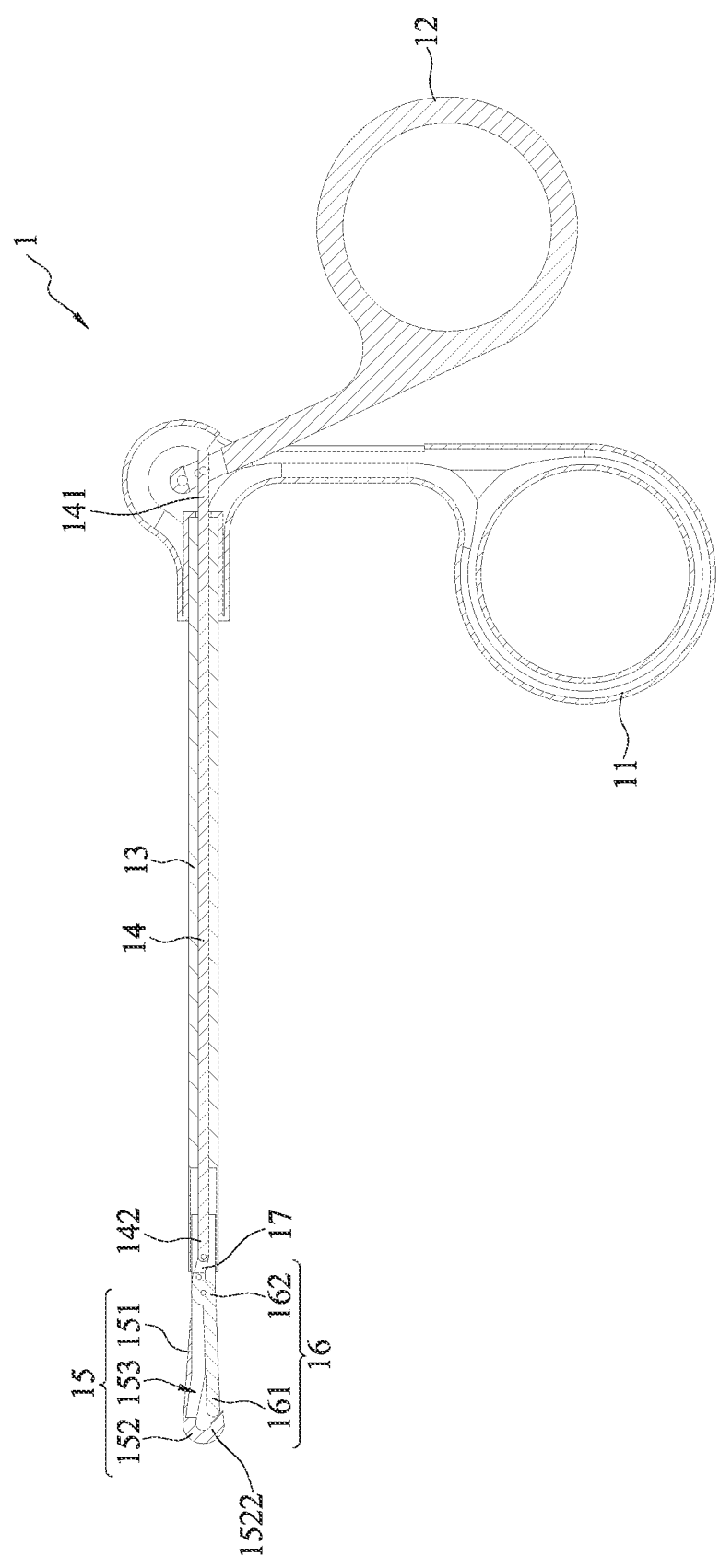
FIG. 1B is a schematic cross-sectional view of FIG. 1A.

FIGS. 1A and 1B are schematic overall and cross-sectional views of the surgical instrument 1 in a first operation state according to the present disclosure. Referring to FIGS. 1A and 1B, the surgical instrument 1 of the present disclosure has a first holding member 11, a second holding member 12, a sleeve member 13, a linkage member 14, a hook member 15 and an opening/closing member 16. One end of the sleeve member 13 is coupled to the first holding member 11. The linkage member 14 is disposed inside the sleeve member 13 and has a first end 141 and a second end 142. The first end 141 is positioned inside the first holding member 11.

In at least one embodiment, the sleeve member 13 is a hollow tubular body, and the linkage member 14 is a rod received in the tubular body of the sleeve member 13. In some embodiments, the linkage member 14 can be, but not limited to, a flexible or rigid wire or spring.

In at least one embodiment, the second holding member 12 is pivotally connected to the first holding member 11 and coupled to the first end 141 of the linkage member 14 so as to allow the linkage member 14 to move back and forth inside the sleeve member 13 when the second holding member 12 moves relative to the first holding member 11.

Referring to FIG. 1B, the hook member 15 has an extending portion 151, a bending portion 152 and a receiving space 153. One end of the extending portion 151 is coupled to one end of the sleeve member 13 that is far away from the first holding member 11. The bending portion 152 extends from the other end of the extending portion 151 to a free end 1522 and bends around an axis extending in the length direction of the linkage member 14 (for example, the free end 1522 of the bending portion 152 may bend toward the first holding member 11). As such, the end of the surgical instrument 1 that is far away from the first holding member 11 and the second holding member 12 is blunt, thereby avoiding the possible injuries resulted from piercing by pushing surgical instrument 1 between tissues during surgery.

Figure 2A:
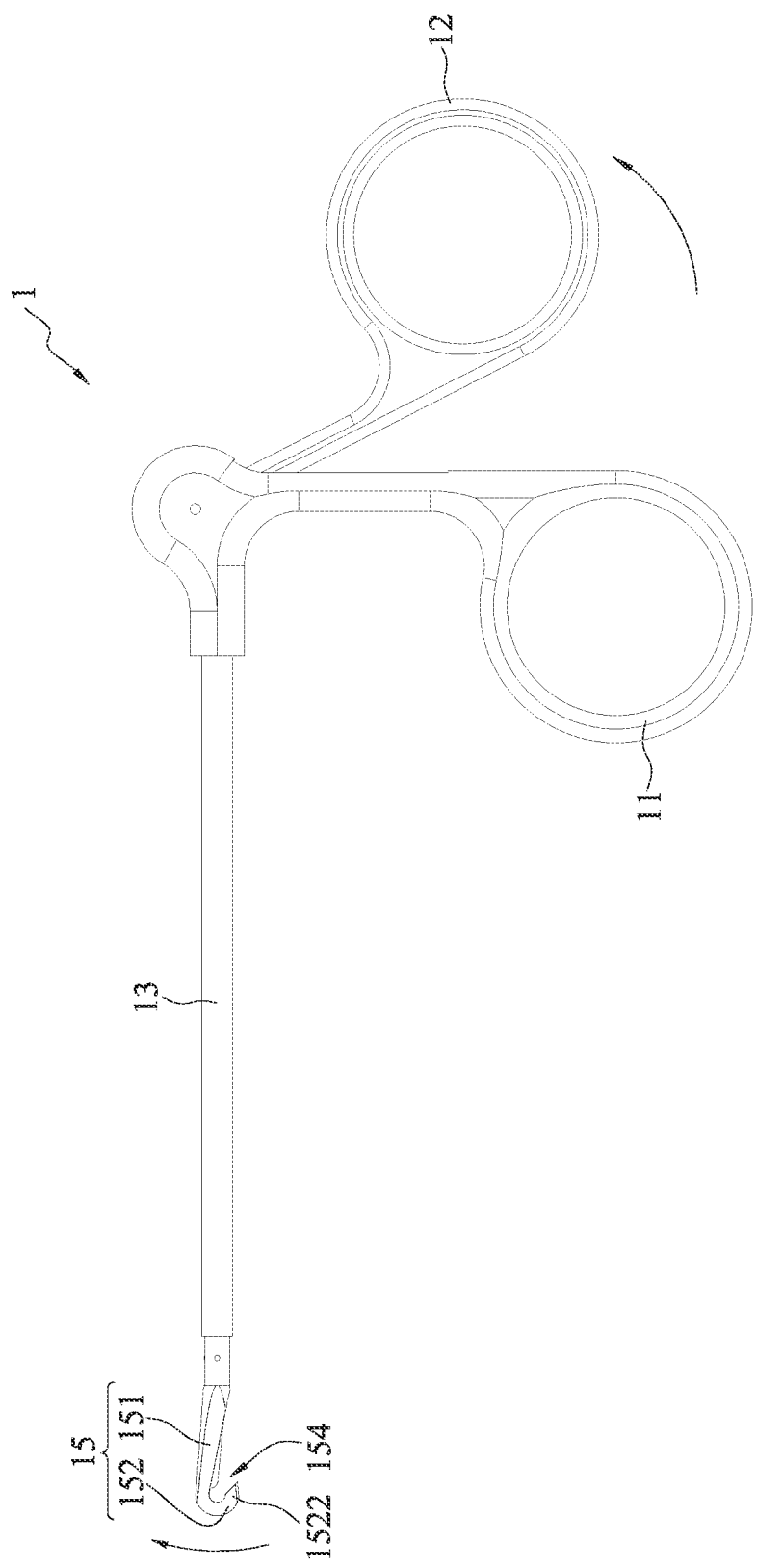
FIG. 2A is a schematic overall view of the surgical instrument in a second operation state according to the present disclosure.
Figure 2B:
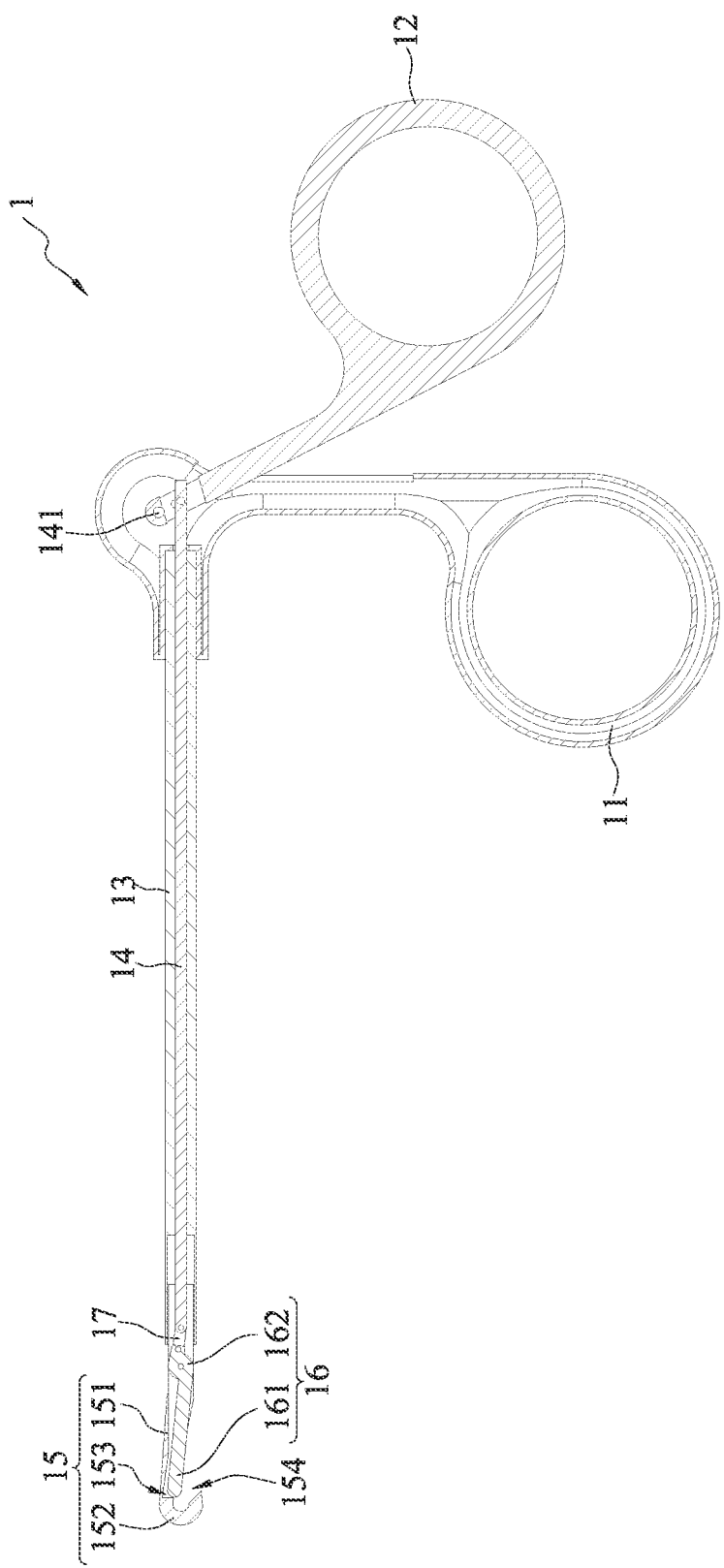
FIG. 2B is a schematic cross-sectional view of FIG. 2A.

In at least one embodiment, referring to FIGS. 2A and 2B, an opening 154 is configured between said one end of the extending portion 151 coupled to the sleeve member 13 and the free end 1522 of the bending portion 152.

In at least one embodiment, one end of the opening/closing member 16 is pivotally connected to the extending portion 151 and connected to the second end 142 of the linkage member 14. Referring to FIGS. 2A and 2B, which show the schematic overall and cross-sectional views of the surgical instrument 1 in a second operation state according to the present disclosure. In FIGS. 1A and 1B, one end of the opening/closing member 16 abuts against the free end 1522 of the bending portion 152. Referring to FIGS. 2A and 2B, when the second holding member 12 moves away from the first holding member 11, the opening/closing member 16 moves toward the extending portion 151. In this state, if the second holding member 12 moves toward the first holding member 11 again, the opening/closing member 16 will move toward the opening 154, as shown in FIGS. 1A and 1B.

In at least one embodiment, when the opening/closing member 16 moves toward the extending portion 151, the opening/closing member 16 can move into the receiving space 153 of the extending portion 151 so as to be received by the receiving space 153. When the opening/closing member 16 moves toward the opening 154, the opening/closing member 16 can move until it abuts against the free end 1522 of the bending portion 152. As such, the opening 154 is closed. Further, the movement of the opening/closing member 16 is achieved through the movement of the linkage member 14. In other words, through the movement of the second holding member 12 relative to the first holding member 11, the linkage member 14 is moved so as to drive the opening/closing member 16 to move between the extending portion 151 and the opening 154.

Figure 6:
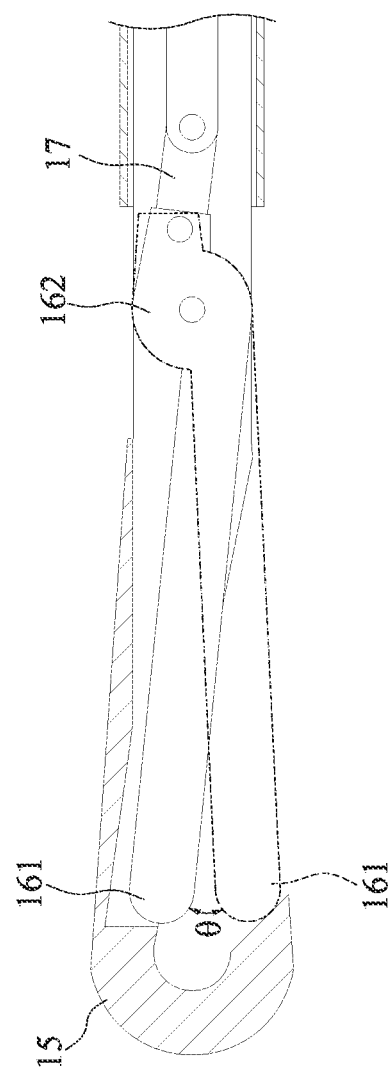
FIG. 6 is a schematic view showing operation of an opening/closing member of the surgical instrument according to the present disclosure.

In at least one embodiment, referring to FIG. 6, the opening/closing member 16 has a pivoting portion 162 pivotally connected to the hook member 15 and an opening/closing portion 161 extending from the pivoting portion 162 along a tangent direction thereof and having a length that allows the opening/closing portion 161 to abut against the free end 1522 of the bending portion 152. Hence, when the pivoting portion 162 rotates relative to the hook member 15, the opening/closing member 16 can move between the receiving space 153 and the opening 154 until it abuts against an inner side of the free end 1522 of the bending portion 152.

In order to achieve rotation of the pivoting portion 162 relative to the hook member 15, the linkage member 14 can be pivotally connected at a position deviating from where the pivoting portion 162 is pivotally connected to the hook member 15. For example, the pivoting portion 162 can have a substantially circular shape, the opening/closing portion 161 can extend in a tangent direction of the circular shape at one end of the diameter of the circular shape, and the linkage member 14 can be pivotally connected at an another end of the diameter different from the extended position of the opening/closing portion 161. However, the present disclosure is not limited thereto.

In at least one embodiment, the movement of the linkage member 14 can be controlled through the position where the linkage member 14 is pivotally connected to the hook member 15, and the opening/closing member 161 can rotate relative to the hook member 15 by an angle within a certain range. The rotation angle θ in the present disclosure can be, but not limited, in a range of 0 to 40 degrees, for example, 0 to 35 degrees, 0 to 32 degrees, 0 to 30 degrees, 0 to 27 degrees, or 0 to 25 degrees.

In some embodiments, referring to FIGS. 2B and 6, a connection member 17 is further provided between the linkage member 14 and the pivoting portion 162. Two ends of the connection member 17 are pivotally connected to the linkage member 14 and to a position deviating from the position where the pivoting portion 162 is pivotally connected to the hook member 15, respectively. The connection member 17 provides buffer so as to maintain the linkage member 14 in an axial direction parallel to the sleeve member 13 and prevent the end of the linkage member 14, which is pivotally connected to the pivoting portion 162, from bending or deforming that otherwise could hinder movement of the linkage member 14 in the sleeve member 13.

Figure 3:
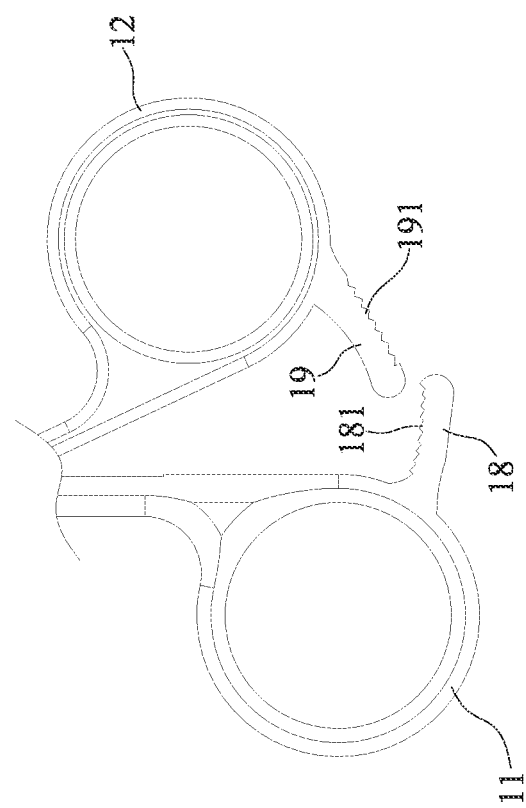
FIG. 3 is a schematic view of a first holding member and a second holding member of the surgical instrument according to an embodiment of the present disclosure.

In at least one embodiment, referring to FIG. 3, the first holding member 11 has a first engaging portion 18, and the second holding member 12 has a second engaging portion 19. The first engaging portion 18 is provided with a first tooth portion 181, and the second engaging portion 19 is provided with a second tooth portion 191. When the second holding member 12 moves toward the first holding member 11, the second tooth portion 191 is engaged with the first tooth portion 181 so as to fix relative positions of the second holding member 12 and the first holding member 11.

Figure 4B:
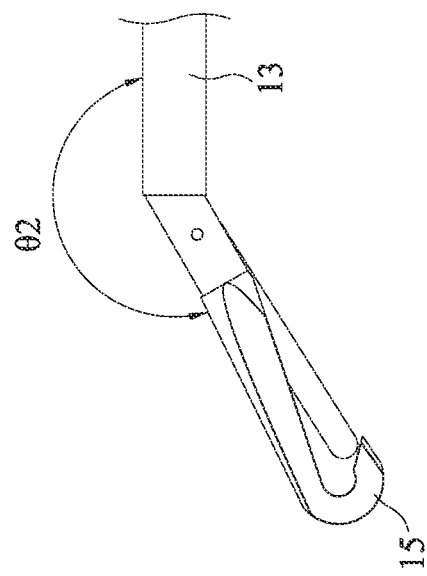
FIGS. 4A and 4B are schematic views of a hook member of the surgical instrument according to an embodiment of the present disclosure.
Figure 4A:
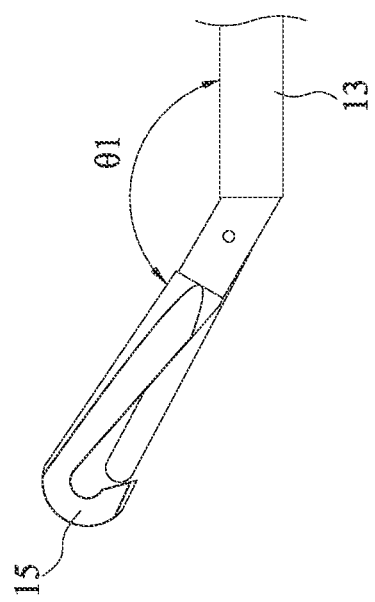
Figure 5A:
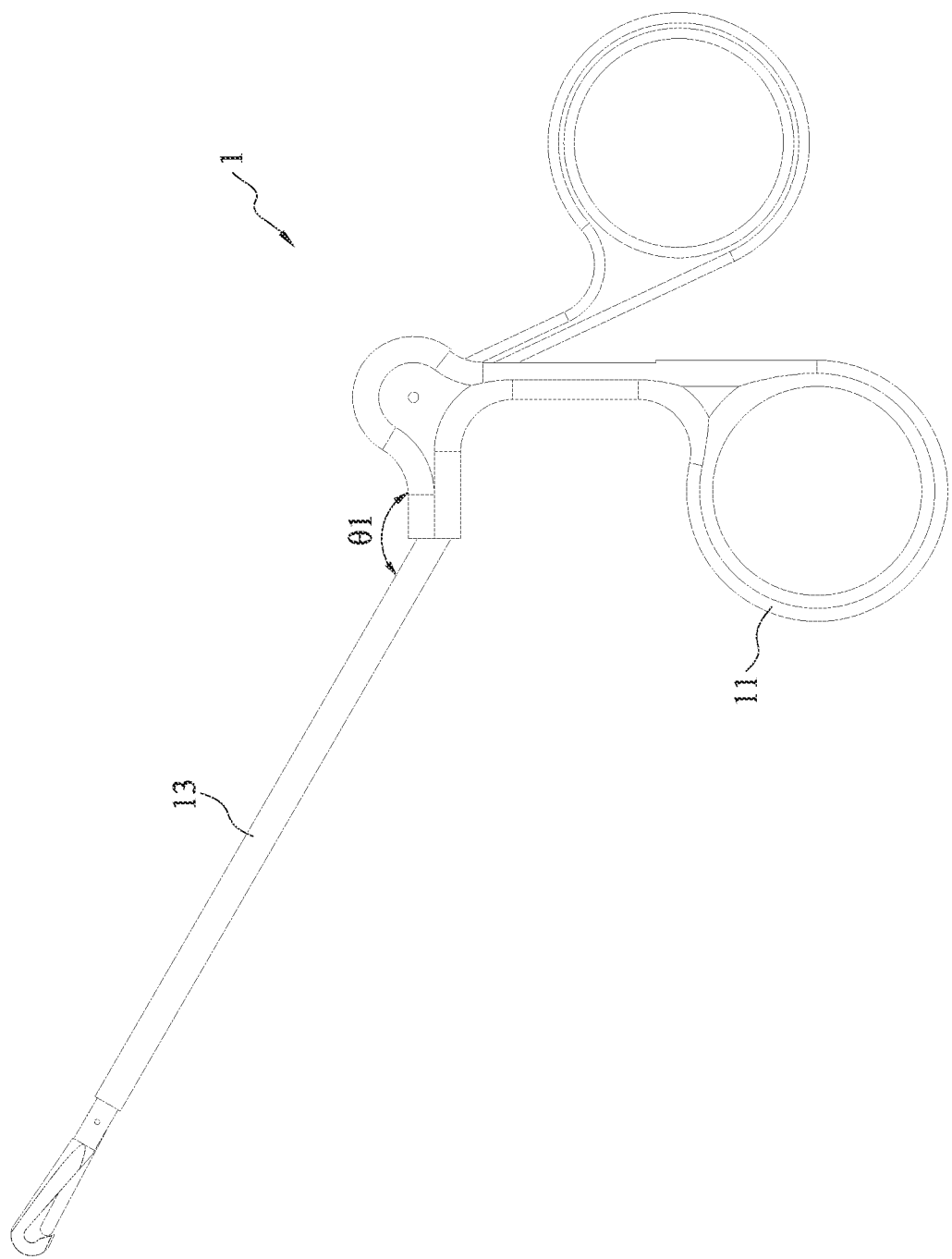
FIGS. 5A and 5B are schematic views of a sleeve member of the surgical instrument according to an embodiment of the present disclosure.
Figure 5B:
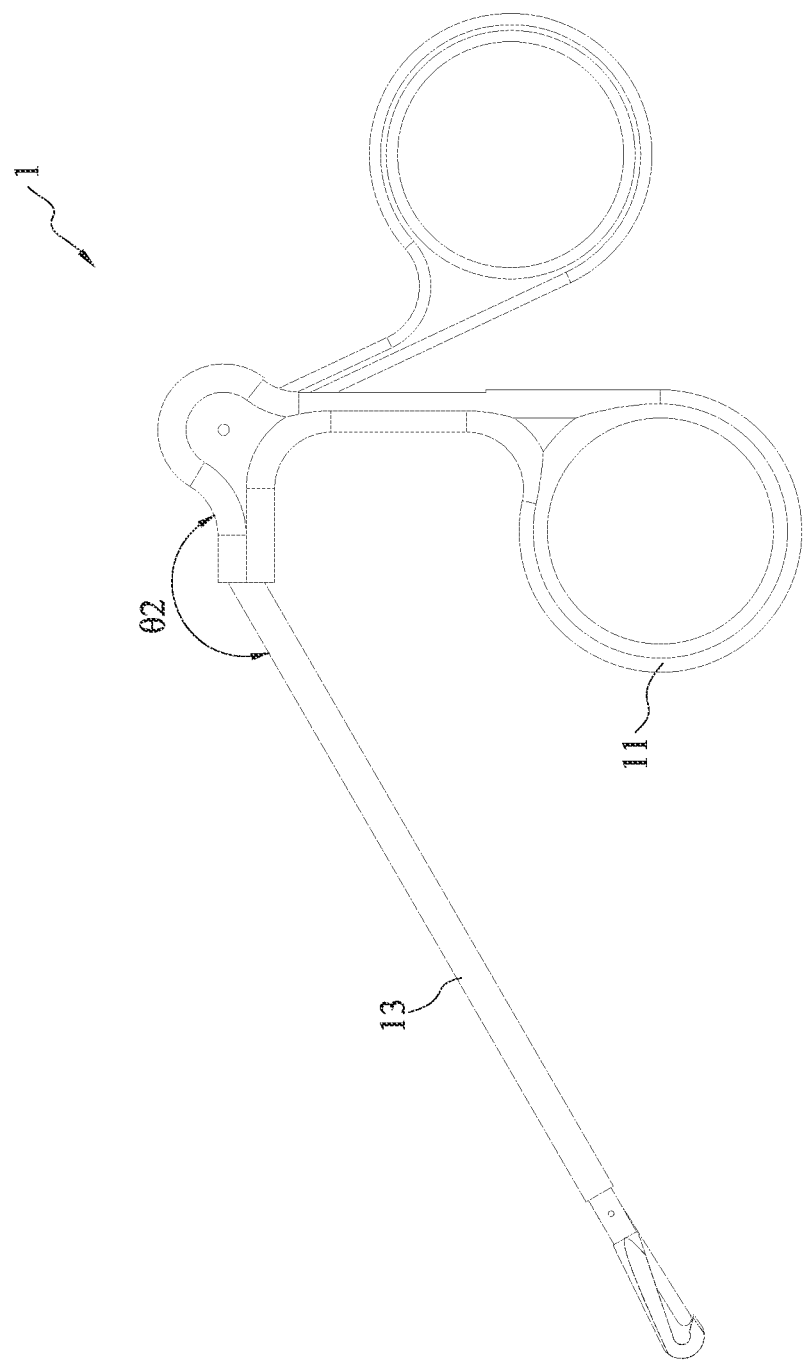

In some embodiments, referring to FIGS. 4A and 4B, the angle between the hook member 15 and the sleeve member 13 is not limited to 180 degrees. For example, the angle θ1 between the hook member 15 and the sleeve member 13 can be 135, 140, 145, 150, 155, 160, 165, 170 or 175 degrees, or the angle θ2 between the hook member 15 and the sleeve member 13 can be 185, 190, 195, 200, 205, 210, 215, 220 or 225 degrees. Further, referring to FIGS. 5A and 5B, the angle between the sleeve member 13 and the first holding member 11 is not limited to 180 degrees. For example, the angle θ1 between the sleeve member 13 and the first holding member 11 can be 135, 140, 145, 150, 155, 160, 165, 170 or 175 degrees, or the angle θ2 between the sleeve member 13 and the first holding member 11 can be 185, 190, 195, 200, 205, 210, 215, 220 or 225 degrees. It should be noted that these angles can be varied according to actual operation sites.

In at least one embodiment, the first holding member 11 and the second holding member 12 are made of plastics for medical use, and the sleeve member is made of plastic or stainless steel for medical use. The first holding member 11 or the second holding member 12 can be two housing bodies bonded to one another (e.g., by screws made of stainless steel) and provided with a ring structure that can be held by fingers. Alternatively, referring to FIGS. 1A to 2B, the first holding member 11 and the second holding member 12 are of a scissor handle shape with only one end pivotally connected. However, the present disclosure is not limited thereto.

In at least one embodiment, the hook member 15 and the opening/closing member 16 are made of stainless steel for medical uses, and the linkage member 14 is made of stainless steel for medical uses. However, the present disclosure is not limited thereto.

Figure 7:
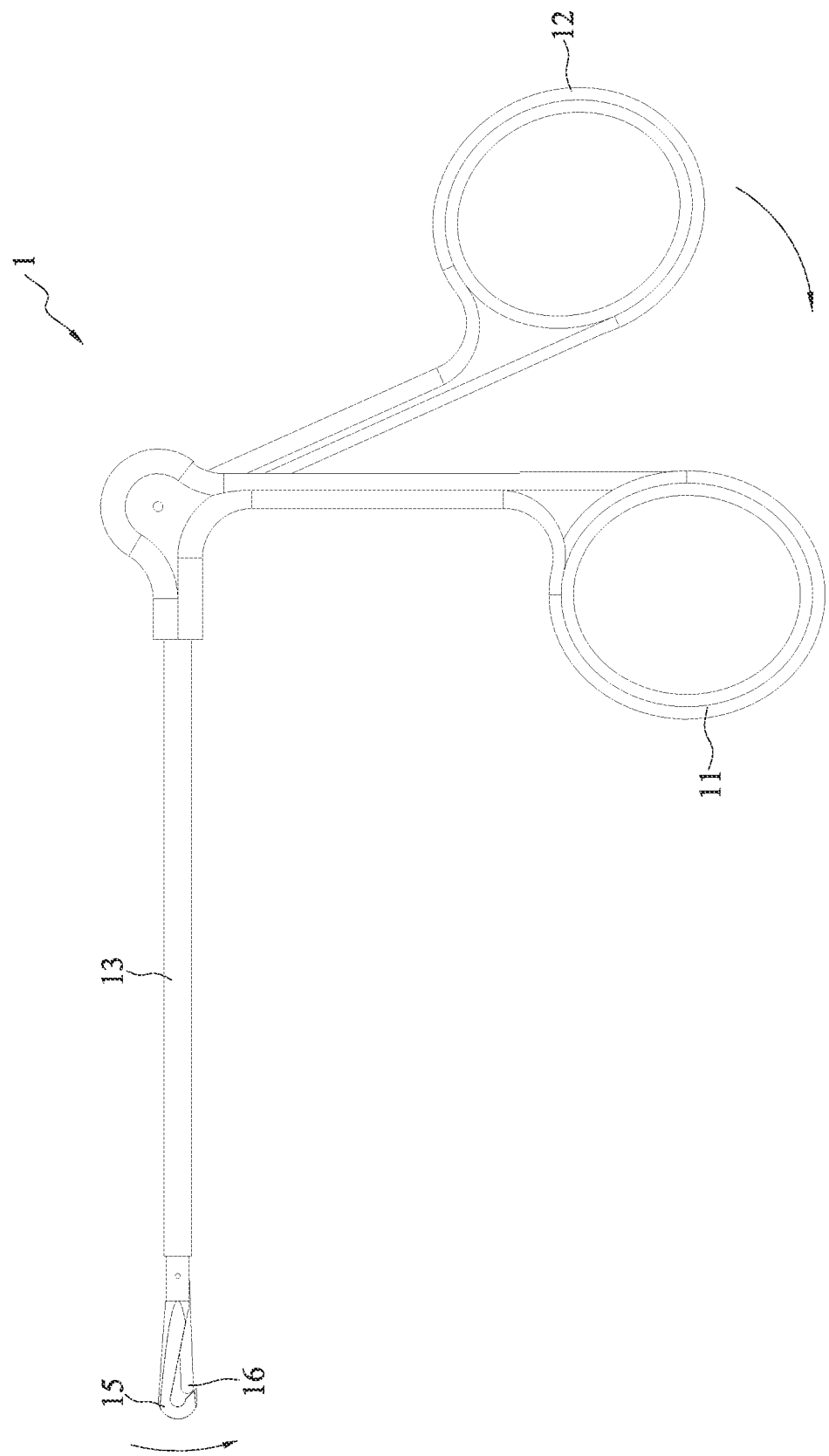
FIG. 7 is a schematic overall view of the surgical instrument according to an embodiment of the present disclosure.

FIG. 7 is a schematic overall view of the surgical instrument according to another embodiment of the present disclosure. This embodiment differs from the above-described embodiment in the design of the first holding member 11 and the second holding member 12. The difference between this embodiment and the others is described as follows, while the same technical characteristics thereof are not reiterated.

In the present embodiment, the first holding member 11 and the second holding member 12 are longer than those of FIG. 1A so as to conform to ergonomics and to facilitate operation. Further, different from the circular shape of FIG. 1A, the circular ring structures of the first holding member 11 and the second holding member 12 of the present embodiment have an elliptical shape.

According to the present disclosure, when the first holding member and the second holding member move relative to one another, the opening/closing member can move between the extending portion and the opening. As such, after a suture is captured by the hook member, the opening can be closed by the opening/closing member, thus preventing the suture from falling off while pushing out the surrounding soft tissues, blood vessels or nerves that have strayed into the opening, especially when the surgical instrument of the present disclosure is used in combination with an ultrasonic device and tissues cannot be clearly identified from an ultrasound image. Therefore, the surgical instrument of the present disclosure overcomes the conventional drawbacks of injuring the surrounding soft tissues, blood vessels or nerves and at least has advantages of short recovery time after surgery, low infection rate, small wound, short operation time, short training time, among others. The surgical instrument of the present disclosure is not necessarily used in combination with ultrasonic imaging devices. Even if the surgical instrument of the present disclosure is used in combination with an endoscope where the surrounding soft tissues, blood vessels or nerves at an operation site can be seen, it still helps doctors to reduce the risk of accidentally injuring the surrounding soft tissues, blood vessels or nerves.

The above-described embodiments only illustrate technical principles, features and effects of the present disclosure, and not intended to limit the scope of the present disclosure. Accordingly, all modifications and variations completed by those with ordinary skill in the art should fall within the scope of the present disclosure defined by the appended claims.

What is claimed is:
1. A surgical instrument, comprising:
a first holding member;
a sleeve member coupled to the first holding member through one end thereof;

a linkage member disposed inside the sleeve member and having a first end and a second end, wherein the first end is positioned inside the first holding member;

a second holding member pivotally connected to the first holding member and coupled to the first end of the linkage member, allowing the linkage member to move inside the sleeve member when the second holding member moves relative to the first holding member;

a hook member comprising an extending portion and a bending portion, wherein one end of the extending portion is coupled to the other end of the sleeve member, and the bending portion extends from the other end of the extending portion and bends inwardly toward the first holding member, and an opening is configured between said one end of the extending portion coupled to the sleeve member and a free end of the bending portion; and an opening/closing member having one end pivotally connected to the extending portion and connected to the second end of the linkage member such that when the linkage member moves, the other end of the opening/closing member moves between the extending portion and the free end within the opening.

2. The surgical instrument of claim 1, wherein when the second holding member moves away from the first holding member, the opening/closing member moves toward the extending portion.

3. The surgical instrument of claim 2, wherein the extending portion further comprises a receiving space recessed inside the extending portion for receiving the opening/closing member.

4. The surgical instrument of claim 1, wherein when the second holding member moves toward the first holding member, the opening/closing member moves toward the opening.

5. The surgical instrument of claim 4, wherein the opening/closing member is configured to move toward the opening until one end of the opening/closing member abuts against the free end of the bending portion.

6. The surgical instrument of claim 1, wherein the opening/closing member comprises a pivoting portion pivotally connected to the hook member and an opening/closing portion extending from the pivoting portion along a tangent direction thereof and having a length that allows the opening/closing portion to abut against the free end of the bending portion.

7. The surgical instrument of claim 6, wherein the linkage member is pivotally connected at a position deviating from the position where the pivoting portion is pivotally connected to the hook member such that when the linkage member moves, the opening/closing portion rotates relative to the hook member by an angle between 0 and 40 degrees.

8. The surgical instrument of claim 7, further comprising a connection member between the linkage member and the pivoting portion, wherein two ends of the connection member are respectively pivotally connected to the linkage member and to the pivoting portion at the position deviating from the position where the pivoting portion is pivotally connected to the hook member, thereby maintaining the linkage member in an axial direction parallel to the sleeve member.

9. The surgical instrument of claim 1, wherein the first holding member comprises a first engaging portion having a first tooth portion, and the second holding member comprises a second engaging portion having a second tooth portion, and wherein when the second holding member moves toward the first holding member, the second tooth portion of the second engaging portion is engaged with the first tooth portion of the first engaging portion.

10. The surgical instrument of claim 1, wherein an angle between the hook member and the sleeve member is in a range of from 135 to 225 degrees.

11. The surgical instrument of claim 1, wherein an angle between the sleeve member and the first holding member is in a range of from 135 to 225 degrees.

12. The surgical instrument of claim 1, wherein the first holding member and the second holding member are made of plastic for medical use, the sleeve member is made of plastic or stainless steel for medical use, the hook member and the opening/closing member are made of stainless steel for medical use, and the linkage member is made of stainless steel for medical use.

13. The surgical instrument of claim 1, wherein the linkage member is a rod, a wire or a spring.

* * * * *